United States Patent [19]

Brown et al.

[11] 3,983,110

[45] Sept. 28, 1976

[54] SUBSTITUTED BENZOPYRANOPYRIDINE

[75] Inventors: Richard E. Brown, East Hanover; Chester Puchalski, Dover; John Shavel, Jr., Mendham, all of N.J.

[73] Assignee: Warner-Lambert Company, Morris Plains, N.J.

[22] Filed: July 25, 1975

[21] Appl. No.: 599,290

Related U.S. Application Data

[63] Continuation-in-part of Ser. No. 534,502, Dec. 19, 1974, Pat. No. 3,946,008, which is a continuation-in-part of Ser. No. 343,613, March 21, 1973, abandoned, which is a continuation-in-part of Ser. No. 122,498, March 9, 1972, abandoned.

[52] U.S. Cl.................. 260/247.2 B; 260/239 B; 260/268 PC; 260/268 TR; 260/243 B

[51] Int. Cl.².................................... C07D 491/04
[58] Field of Search............ 260/247.2 B, 247.1 L, 260/268 PC, 268 TR

[56] References Cited
FOREIGN PATENTS OR APPLICATIONS
2,351,734   4/1974   Germany ................. 260/247.2

Primary Examiner—Paul J. Killos
Attorney, Agent, or Firm—Albert H. Graddis; Frank S. Chow; George M. Yahwak

[57] ABSTRACT

Disclosed is a novel substituted benzopyranopyridine which is active as a bronchodilator agent.

4 Claims. No Drawings

SUBSTITUTED BENZOPYRANOPYRIDINE

This application is a continuation-in-part of our application Ser. No. 534,502, filed Dec. 19, 1974, now U.S. Pat. No. 3,946,008 the disclosure of which is hereby incorporated by reference, which is in turn a continuation-in-part of our application Ser. No. 343,613, filed Mar. 21, 1973, now abandoned the disclosure of which is hereby incorporated by reference, which is in turn a continuation-in-part of our application Ser. No. 122,498, filed Mar. 9, 1971 and now abandoned.

This invention relates to novel substituted benzopyranopyridines of the formula I.

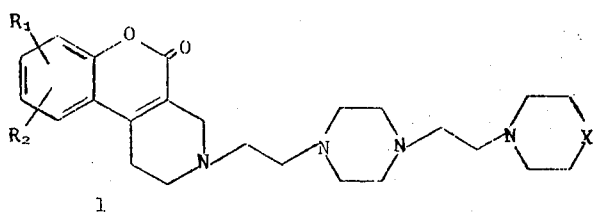

In the above formula, $R_1$ and $R_2$ may be hydrogen, hydroxy, lower alkoxy or lower alkyl of 1 to 6 carbon atoms or may be taken together to form a methylenedioxy group. X may be oxygen, sulfur, $CH_2CH_2$, a bond connecting the adjacent carbon atoms, or $CH-R_3$ or $N-R_3$ wherein $R_3$ may be hydrogen or lower alkyl of 1 to 6 carbon atoms.

The compounds of this invention are prepared by reacting a substituted benzopyranopyridine of structure II with a suitable alkylating agent of structure III. In structure II, $R_1$ and $R_2$ are as defined for I. In structure III, hal. refers to halogen and may be chlorine, bromine or iodine.

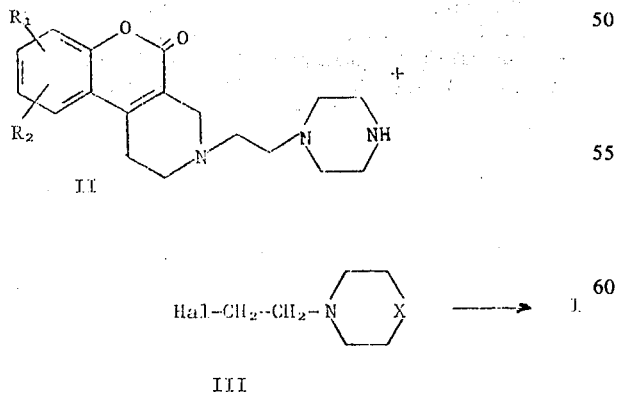

The starting materials according to structure II are described in our co-pending application Ser. No. 534,502. The alkylation reactions are carried out in a suitable solvent in the presence of a base to serve as proton acceptor. Among the solvents which may be used are alcohols of 1 to 6 carbon atoms such as methanol, ethanol or amyl alcohol; polar aprotic solvents as dimethylformamide, dimethylsulfoxide and the like, tetrahydrofuran and dioxane. Suitable bases are potassium carbonate, sodium acetate or triethylamine and the like.

The alkylating agents according to structure III are known compounds which are commercially available.

The following examples are given in order to further illustrate the invention:

EXAMPLE 1

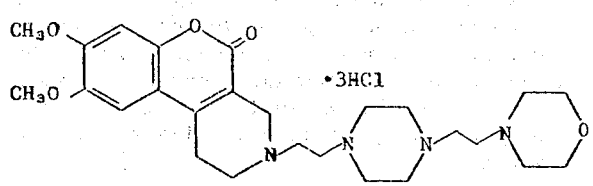

1,2,3,4-Tetrahydro-8,9-dimethoxy-3-(2-[4-(2-morpholinoethyl)-1-piperazinyl]ethyl)-5H-[1]benzopyrano[3,4-c]pyridin-5-one trihydrochloride. A mixture of 0.01m of 3-[2-(1-piperazinyl)ethyl]-1,2,3,4-tetrahydro-8,9-dimethoxy-5H-[1]benzopyrano[3,4-c]pyridin-5-one, 0.011m of N-2-chloroethylmorpholine and 0.011m of triethylamine in 200ml of ethanol was refluxed for 6 hours. The mixture was filtered while hot and treated immediately with excess HCl gas. Recrystallization of the crude product from 4:1 methanol-water afforded pure material, m.p. 262°–4° C.

Anal. Calcd. for $C_{26}H_{38}N_4O_5$·3HCl: C, 52.40; H, 6.93; N, 9.40; Cl, 17.85. Found: C, 50.39; H, 6.92; N, 9.36; Cl, 18.26.

EXAMPLE 2

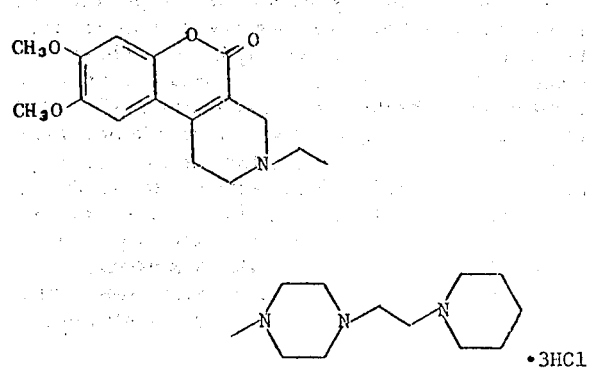

1,2,3,4-Tetrahydro-8,9-dimethoxy-3-{2-[4-(2-piperidinoethyl)-1-piperazinyl]-ethyl}-5H-[1]benzopyrano[3,4-c]pyridin-5-one trihydrochloride. In the same way as described in example 1, 3-[2-(1-piperazinyl ethyl]-1,2,3,4-tetrahydro-8,9-dimethoxy-5H-[1]benzopyrano[3,4-c]pyridin-5-one was alkylated with 2-chloroethylpiperidine. The product was recrystallized from 4:1 methanol-water, m.p. 251°–3° C.

Anal. Calcd. for $C_{27}H_{40}N_4O_4$·3HCl: C, 54.3; H, 7.3; N, 9.4; Cl, 17.8. Found: C, 52.70; H, 7.45; N, 9.71; Cl, 18.64.

EXAMPLE 3

TEST ANIMAL: Male albino guinea pigs (250–350 gm)
ROUTE OF ADMINISTRATION: Intraperitoneal
DOSES: 25 mg/kg
SPASMOGENS: Histamine; 0.1%
PROCEDURE: Pigs are continuously exposed to a spasmogen for 10 min.; delivery is by means of two 0 nebulizers (each nebulizer dispenses 0.2 cc/min.) positioned at the back of a closed, six unit plexiglas chamber (19 × 12½ × 9 in.) and driven by an air pressure of 10 lbs/in$^2$. The time from onset of the aerosol treatment to collapse of each animal is recorded; means values for drug treated animals are compared to those of animals treated with vehicle. Guinea pigs that do not collapse during the 10 min. period are removed from the chamber and a maximum score of 10 is recorded. Test compounds (25 mg/kg, i.p.) are given 15 min. before exposure to spasmogen.

(See Siegmund, O.H. et al.: J. Pharmacol and Exptl. Therapeutics, 90: 254, 1949).

In animal tests for bronchodilation activity according to Example 3, for example, showed marked activity as seen in Table I below:

TABLE I

| DOSE | NO. ANIMALS | COLLAPSE TIME (MIN.) |
| --- | --- | --- |
| control (Example 1) | 3 | 2.2 |
| 25 mg (Example 1) | 3 | 10.0 |

The compounds according to this invention are bronchodilator agents and protect the guinea pig against bronchospasm for a duration up to four hours at an oral dose of 10 mg/kg. The compound of Example 1 is more effective against bronchospasm than aminophylline, a commercial product used in the treatment of bronchial asthma and pulmonary edema, which protects the guinea pig against identical bronchospasm for less than two hours at a dose of 100 mg/kg. In addition, the compounds reverse pilocarpine or histamine bronchoconstriction in the dog for a duration of up to 1 hour at an oral dose of 10 mg/kg. The bronchodilator activity exhibited by the N-substituted benzopyrano[3,4-c]pyridine described in this invention is the result of a direct smooth muscle relaxant effect on the bronchial tree as shown by in vitro experiments on guinea pig trachea. In these experiments, the N-substituted benzopyrano[3,4-c]pyridine is many times more active than aminophylline in relaxing tracheal smooth muscle.

The compounds of this invention are useful for the treatment of bronchial asthma. Generally speaking, a dose of about 500 mg to 1000 mg several times daily is recommended for mammals weighing about 70 kilograms. The compounds can be administered orally or by parenteral administration.

In order to use these compounds they are formulated with pharmaceutically acceptable excipients such as lactose, starch, powdered sugar and the dosage forms can be tablets, capsules and the like. The dosage regimen can be varied according to the condition being treated by methods well known to the healing arts.

We claim:
1. A benzopyranopyridine of the general formula:

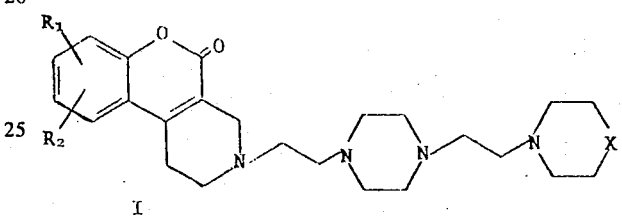

I wherein $R_1$ and $R_2$ may be hydrogen, hydroxy, lower alkoxy or lower alkyl of 1 to 6 carbon atoms or may be taken together to form a methylenedioxy group; X may be oxygen, sulfur, $CH_2CH_2$, a bond connecting the adjacent carbon atoms, CH—$R_3$ or N—$R_3$ wherein $R_3$ may be hydrogen or lower alkyl of 1 to 6 carbon atoms; or the hydrochloride salts thereof.

2. A benzopyranopyridine according to claim 1 wherein $R_1$ is a lower alkoxy; $R_2$ is a lower alkoxy; and X is an oxygen or —$CH_2$— radical.

3. The benzopyranopyridine according to claim 2 which is 1,2,3,4-tetrahydro-8,9-dimethoxy-3-(2-[4-(2-morpholinoethyl)-1-piperazinyl]ethyl)-5H-[1]benzopyrano[3,4-c]pyridin-5-one trihydrochloride.

4. The benzopyranopyridine according to claim 2 which is 1,2,3,4-tetrahydro-8,9-dimethoxy-3-{2-[4-(2-piperidinoethyl)-1-piperazinyl]-ethyl}-5H-[1]benzopyrano[3,4-c]pyridin-5-one trihydrochloride.

* * * * *